United States Patent
Sasaki et al.

(10) Patent No.: US 6,926,392 B2
(45) Date of Patent: Aug. 9, 2005

(54) LIQUID EJECTION HEAD

(75) Inventors: Toshiaki Sasaki, Yokohama (JP); Keiichi Murai, Tokyo (JP); Yasuyuki Tamura, Yokohama (JP); Sadayuki Sugama, Tsukuba (JP); Akira Asai, Atsugi (JP); Tsutomu Kawai, Yokohama (JP); Masayoshi Tachihara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/620,421

(22) Filed: Jul. 17, 2003

(65) Prior Publication Data

US 2005/0073556 A1 Apr. 7, 2005

Related U.S. Application Data

(63) Continuation of application No. PCT/JP02/12235, filed on Nov. 22, 2002.

(30) Foreign Application Priority Data

| Nov. 22, 2001 | (JP) | ........................................ 2001-358291 |
| Nov. 22, 2001 | (JP) | ........................................ 2001-358292 |
| Nov. 22, 2001 | (JP) | ........................................ 2001-358293 |

(51) Int. Cl.$^7$ .................................................. B41J 2/05
(52) U.S. Cl. ......................................... 347/65; 347/94
(58) Field of Search ............................ 347/20, 44, 46, 347/47, 54, 56, 61, 63, 92–94, 65, 67

(56) References Cited

U.S. PATENT DOCUMENTS

| 5,754,202 | A | | 5/1998 | Sekiya et al. | ................... 347/63 |
| 5,821,962 | A | * | 10/1998 | Kudo et al. | ................... 347/65 |
| 6,007,187 | A | * | 12/1999 | Kashino et al. | ................ 347/65 |
| 6,113,224 | A | | 9/2000 | Sugama et al. | ................ 347/65 |
| 6,164,763 | A | | 12/2000 | Sugama et al. | ................ 347/63 |
| 6,350,016 | B1 | | 2/2002 | Tachihara et al. | .............. 347/56 |
| 6,386,832 | B1 | | 5/2002 | Taneya et al. | ................. 347/65 |
| 6,409,317 | B1 | | 6/2002 | Shimazu et al. | ............... 347/65 |
| 6,450,776 | B1 | | 9/2002 | Taneya et al. | ................. 347/65 |
| 6,457,816 | B1 | * | 10/2002 | Ishinaga et al. | ............... 347/65 |

FOREIGN PATENT DOCUMENTS

| JP | 5-77422 | 3/1993 | ............. B41J/2/05 |
| JP | 5-193141 | 8/1993 | ............. B41J/2/135 |
| JP | 11-334069 | 12/1999 | ............. B41J/2/045 |

* cited by examiner

*Primary Examiner*—Juanita D. Stephens
(74) *Attorney, Agent, or Firm*—Fitzpatrick, Cella, Harper & Scinto

(57) ABSTRACT

A liquid ejection head includes a liquid path; an ejection outlet forming member which constitutes a part of a wall of the liquid and which forms an ejection outlet for ejecting a droplet of liquid; a heat generating element, provided at a position opposing to the ejection outlet of the wall of the liquid flow path, for generating a bubble in the liquid by application of heat to the liquid; a restrictor portion, provided at a recessed portion of the ejection outlet, wherein the recessed portion is recessed from a plane in which the ejection outlet is formed, wherein the liquid forms a meniscus and is retained in the ejection outlet such that the restrictor portion is within the liquid, wherein an area So of an opening of the restrictor portion and a surface Sh of the heat generating element satisfy So$\leq$Sh. According to this invention, a central portion of the meniscus opposed to the fine opening at the ejection outlet bulges, and the liquid is ejected in this state. Namely, very small amount of the liquid can be ejected, since not all of the liquid in the recess portion in the ejection outlet is ejected.

12 Claims, 4 Drawing Sheets

LIQUID EJECTION HEAD

This application is a continuation application of pending International Application No. PCT/JP02/12235, filed on Nov. 22, 2002.

TECHNICAL FIELD

The present invention relates to a liquid ejection head for ejecting liquid, in the form of a minute liquid droplet. A liquid ejection head is preferably employed as an ink jet head in the field of ink jet recording for ejecting recording ink. It is also preferably employed, in the field of medicine, as the liquid ejection head of an inhaling apparatus, or the like, used for atomizing liquid medicine so that the medicine can be inhaled into lungs.

BACKGROUND ART

A liquid ejection head for ejecting liquid, in the form of a minute liquid droplet, has been widely employed as an ink jet head in the field of ink jet recording. Not only is an ink jet head required to simply eject liquid droplets, but also it is required to be stable in the direction in which liquid droplets are ejected. Thus, various proposals have been made to meet these requirements.

For example, Japanese Laid-open Patent Application 5-77422 discloses an ink jet head in which, in order to stabilize ink flight, ejection outlets for ejecting ink are placed in recesses, one for one, being in the center of the bottom of the recess to prevent the body of ink from a given ejection outlet from coming into contact with the body of ink from the ejection outlet adjacent thereto. Japanese Laid-open Patent Applications 5-193141 and 11-334069 also disclose an ink jet head in which ejection outlets are placed in recesses, one for one, being in the center of the bottom of the recess. In the case of this ink jet bead, the internal surface of the recess is treated to give it a strong affinity for ink, and the outward surface or the member having the ejection outlet member is treated to cause it to repel ink. This combination of the structural arrangement and surface treatments is intended to form a meniscus in the recess of the ejection outlet so that ink is rejected with the presence of the meniscus in the recess of the ejection outlet. This, according to the aforementioned applications, improves recording quality by stabilizing liquid ejection.

In recent years, the demand has further increased for improving an ink jet head in terms of image quality, in particular, in terms of graininess. Thus, in order to make as inconspicuous as possible the graininess resulting from the manner in which the ink droplets adhere to recording medium, a substantial amount of effort has been made to reduce the size of the droplet in which liquid is ejected. However, the above described ink jet head in accordance with the prior arts are not necessarily structured to substantially reduce liquid droplet size.

The primary object of the present invention is to provide a liquid ejection head which ejects extremely small liquid droplets, more specifically, liquid droplets, the sizes of which are on the order of no more than a pico-liter. Once a liquid ejection head capable of ejecting liquid droplets, the sizes of which are on the order of no more than a pico-liter, is realized, not only will the application or such a liquid ejection head quickly spread in the field of ink jet recording, but also it will spread into fields other than the field of ink jet recording.

According to an aspect of the present invention, there is provided a liquid ejection head comprising a liquid path; an ejection outlet forming member which constitutes a part of a wall of the liquid and which forms an ejection outlet for ejecting a droplet of liquid; a heat generating element, provided at a position opposing to said ejection outlet of the wall of said liquid flow path, for generating a bubble in the liquid by application of heat to the liquid; a restrictor portion, provided at a recessed portion of said ejection outlet, wherein said recessed portion is recessed from a plane in which said ejection outlet is formed, wherein the liquid forms a meniscus and is retained in said ejection outlet such that said restrictor portion is within the liquid, wherein an area So of an opening of said restrictor portion and a surface Sh of said heat generating element satisfy $So \leq Sh$.

According to another aspect of the present invention, there is provided a liquid ejection head comprising a liquid path; an ejection outlet forming member which constitutes a part of a wall of the liquid and which forms an ejection outlet for ejecting a droplet of liquid; an energy generating element, provided at a position opposing to said ejection outlet of the wall of said liquid flow path, for generating ejection energy to be applied to the liquid; a restrictor portion, provided at a recessed portion of said ejection outlet, wherein said recessed portion is recessed from a plane in which said ejection outlet is formed, wherein the liquid forms a meniscus and is retained in said ejection outlet such that said restrictor portion is within the liquid, wherein a thickness c or said restrictor portion and a height e of said liquid path measured in a direction in which said ejection outlet and said energy generating element are faced to each other, satisfy $c \leq e$.

According to a further aspect of the present invention, there is provided a liquid ejection head comprising a liquid path; an ejection outlet forming member which constitutes a part of a wall of the liquid and which forms an ejection outlet for ejecting a droplet of liquid; an energy generating element, provided at a position opposing to said ejection outlet of the wall of said liquid flow path, for generating ejection energy to be applied to the liquid; a restrictor portion, provided at a recessed portion of said ejection outlet, wherein said recessed portion is recessed from a plane in which said ejection outlet is formed, wherein the liquid forms a meniscus and is retained in said ejection outlet such that said restrictor portion is within the liquid, wherein a thickness c of said restrictor portion and a thickness d of said ejection outlet forming member measured between a plane in which said ejection outlet is formed and said restrictor portion, satisfy $c \leq d$.

The position of the restrictor portion in the ejection outlet, in terms of the thickness direction of the member having the energy generating members is desired to be between the top and bottom surfaces of the member. Also, the hole of the restrictor portion is tapered so that the top opening of the hole is greater than that of the bottom opening of the hole, or vice versa. Further, the restrictor portion is desired to have a plurality of holes, as liquid passages, smaller than the other portions of the ejection outlet.

As for examples of liquid ejectable from a liquid ejection head, there are recording liquids used for ink jet recording, liquid medicines inhaled into lungs, etc.

DISCLOSURE OF THE INVENTION

In a liquid ejection head such as the above described one, prior to the beginning of ejection, the outward opening of each ejection outlet of the member having the ejection outlets is covered with the meniscus formed by the liquid in the head, with the small hole of the restrictor portion being in the liquid in the head. Then, as the heat generating element is driven to eject liquid, a bubble is generated, and the bubble grows while moving the liquid toward at least, the outward opening of the ejection outlet. As the liquid is moved toward the outward opening of the ejection outlet, it is forced through the small hole of the restrictor portion, being thereby substantially increased in speed as it is moved through the small hole. Therefore, the speed at which the liquid moves after being moved through the small hole of the restrictor portion is much faster than prior to its passage through the small hole. As a result, the portion of the ink in the recess of the ejection outlet, which corresponds in position to the small hole of the restrictor portion, is moved faster than the body of ink surrounding this portion of ink.

As a result, this fast moving portion of liquid causes the center portion, that is, the portion corresponding in position to the small hole of the restrictor portion, of the meniscus covering the outward opening of the ejection outlet, to swell up, and eventually, it ejects in the form of a liquid droplet. In this case, the entirety of the body of ink in the recess, or the large diameter portion, of the ejection outlet is not ejected. Therefore, the liquid ejection head in accordance with the present invention can eject liquid droplets, which are much smaller in size compared to those ejected by a liquid ejection head in accordance with the prior arts. Further, a certain amount of liquid remains in the recess, that is, the large diameter portion of the ejection outlet, keeping the small hole of the restrictor portion in the liquid. Therefore, the problem that the small hole of the restrictor portion becomes plugged as the liquid therein dries up, docs not occur. Thus, preferable liquid droplets can be ejected from the very beginning of a liquid ejection operation.

These and other objects, features, and advantages of the present invention will become more apparent upon consideration of the following description of the preferred embodiments of the present invention, taken in conjunction with the accompanying drawings.

BEST MODE FOR CARRYING OUT THE INVENTION

Hereinafter, the embodiments of the present invention will be described with reference to the appended drawings.

Figure 1A:
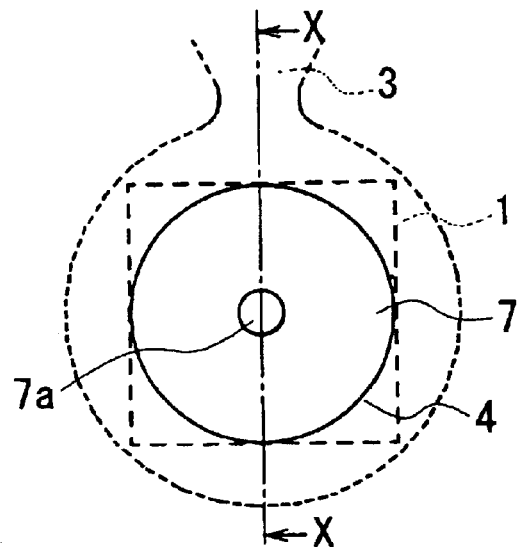
FIG. 1A is a plan view of the liquid ejection head in an embodiment of the present invention.
Figure 1B:
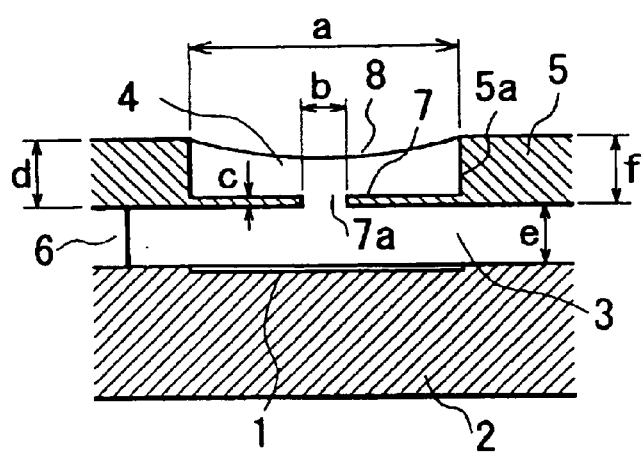
FIG. 1B is a sectional view thereof, at plane x—x in FIG. 1A.
Figure 2A:
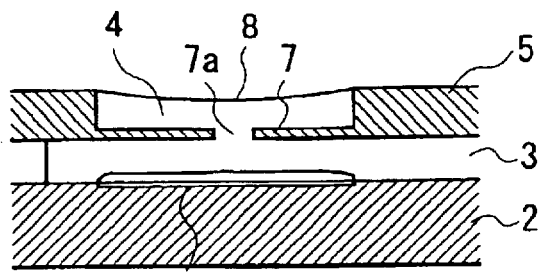
FIGS. 2A, 2B, 2C and 2D are drawings for showing how liquid is ejected in the form of a liquid droplet as the head shown in FIGS. 1A and 1B is driven.
Figure 2B:
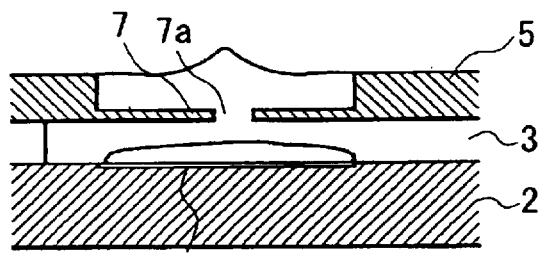
Figure 2C:
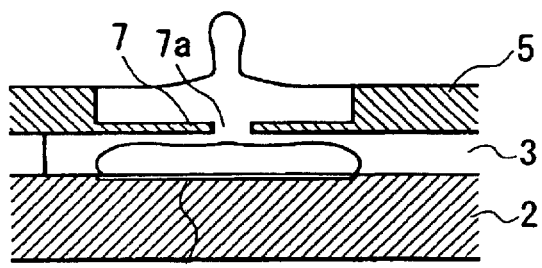
Figure 2D:
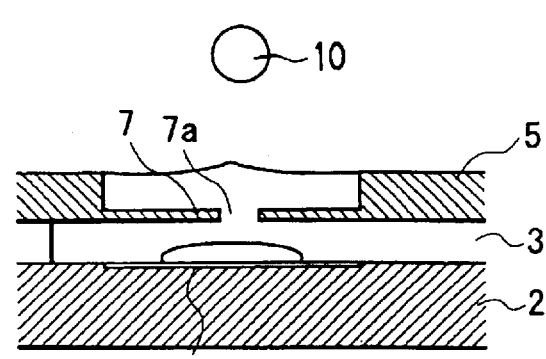

FIG. 1 shows the liquid ejection head in an embodiment or the present invention, FIG. 1(a) being a plan view thereof, and FIG. 1(b) being a sectional view thereof, at the plane X—X in FIG. 1(a).

The liquid ejection head shown in FIG. 1 comprises a substrate 2, and a heater 1, as an element for generating the energy for liquid ejection. The heater 1 is disposed in the liquid path. Although FIG. 1 shows the combination of one heater 1 and one liquid path 3, there are disposed a plurality of the heaters 1, one for each liquid path 3, on a single piece of substrate 2. The choice of the energy generating element does not need to be limited to an electrothermal transducing element. For example, it may be a vibratory energy generating element such as a piezoelectric element.

Each liquid path 3 in surrounded by an ejection outlet plate 5 having the ejection outlets 4 through which liquid is ejected in the form of a liquid droplet, the substrate 2, and a gap regulating member 6 for regulating the distance between the ejection outlet plate 5 and substrate 2.

The ejection outlet is provided with a restrictor portion 7, at which the ejection outlet diameter is substantially smaller than at the other portions, at a position recessed from an ejection outlet plane 5b where the ejection outlet 4 opens in the ejection plate 5. Thus, the liquid to be ejected is held in the recess formed by the internal surface 5a of the larger diameter portion of the ejection outlet and the restrictor portion 7, forming a meniscus 8 across the outward opening of the ejection outlet. Therefore, the restrictor portion 7 is in the liquid between the liquid path 3 and the ejection outlet plate 5a of the ejection outlet plate 5.

At this time, the concrete measurements of the liquid ejection head shown in FIG. 1 will be given.

The heater 1 is square, and each edge is 10 $\mu$m long. As for the measurements of the ejection outlet 4, its diameter is 10 $\mu$m at the ejection outlet plane 5a (diameter a), and 3 $\mu$m at the bottom opening; in other words, the diameter b of the small hole 7a of the restrictor portion 7 is 3 $\mu$m. The thickness c of the restrictor portion 7 is 1 $\mu$m. The distance d from the top surface of the restrictor portion 7 to the ejection outlet plane 5a of the ejection outlet plate 5 is 4 $\mu$m, and the height e of the liquid path 3 (height of distance regulating member) is 5 $\mu$m. The thickness f or the ejection outlet plate 6 is 5 $\mu$m.

In a liquid ejection head in accordance with the present invention, the area size So of the small hole 7a and the surface area size Sh of the heater 1 satisfy the following relationship: So$\leq$Sh. To describe more concretely, in the case of the liquid ejection head shown in FIG. 1, Sh=100 $\mu$m$^2$, and So=7.07 $\mu$m$^2$, satisfying: So$\leq$Sh. Also in a liquid ejection head in accordance with the present invention, the thickness c of the restrictor portion 7 and the height e of the liquid path 3 satisfy the following relationship: c$\leq$e. In the case of the liquid ejection head shown in FIG. 1, c=1 $\mu$m, and e=5 $\mu$m, satisfying therefore: c$\leq$e. Also in the case of a liquid ejection head in accordance with the present invention, the thickness c of the restrictor portion 7 and the distance d from the top surface of the restrictor portion 7 to the ejection outlet plane of the ejection outlet plate 5 satisfy the following relationship: c$\leq$d. In the case of the liquid ejection outlet head shown in FIG. 1, c=1 $\mu$m, and d=4 $\mu$m, as mentioned above, satisfying therefore: c$\leq$d.

Next, the liquid ejecting operation of the above described liquid ejection head will be described. FIG. 2 shows how liquid is ejected as the head structured as shown in FIG. 1 is driven.

Referring to FIG. 1, before the liquid ejection head begins to be driven, there is the meniscus 8 covering the outward opening of each ejection outlet 4 of the ejection outlet plate 5, and therefore, the small hole 7a of the restrictor portion 7 is in the liquid. Next, referring to FIG. 2(a), as voltage is applied to the heater 1 for liquid ejection, the heater 1 generates heat, heating the liquid in the liquid path 3, which is in contact with the surface of the heater 1. As a result, the liquid boils in the film-boiling fashion, generating bubbles.

As the bubbles are generated, the bubbles rapidly grow in volume, causing thereby a part of the liquid to move downstream (toward ejection outlet 4) and the other part to move upstream (toward liquid supply side). As the part of the liquid moves toward the ejection outlet 4, it passes through the small hole 7a of the restrictor portion 7, and as it passes through the small hole 7a, it is substantially accelerated. As a result, the portion of the liquid in the aforementioned recess of the ejection outlet 4, corresponding in portion to the small hole 7a, is moved relatively faster than the liquid surrounding this portion corresponding in position to the small hole 7a.

Consequently, the center portion of the meniscus 8 covering the outward opening of the ejection outlet, which corresponds in position to the small hole 7a, is thrust upward by the above described faster moving liquid, which corresponds in position to the small hole 7a. As a result, a liquid droplet 10 is ejected. In this case, the entire body of the ink in the recess of the ejection outlet 4 is not ejected; in other words, a liquid droplet, the volume of which is extremely small (0.014 pl) is ejected. Further, the substantial amount of the body of the liquid in the recess of the ejection outlet 4 remains in the recess. Therefore, the small hole 7a remains within the liquid, being thereby prevented from suffering from the problem that it becomes plugged as the liquid therein dries up. Thus, the liquid ejection head structured as described above can eject desirable liquid droplets from the very beginning of a liquid ejecting operation.

Figure 3:
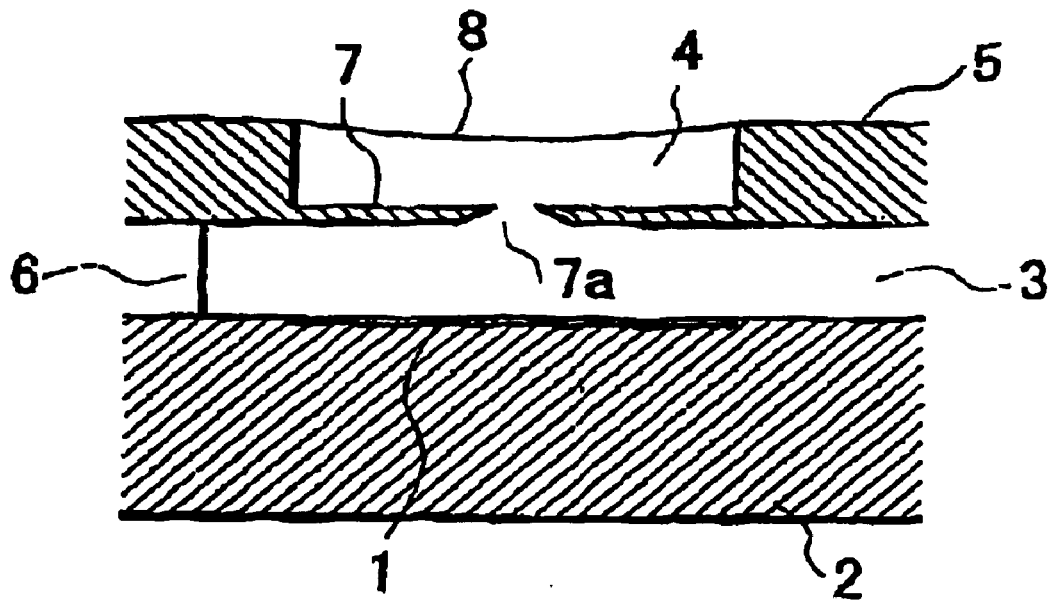
FIG. 3 is a sectional view or the first modified version of the liquid ejection head shown in FIG. 1.

FIG. 3 shows the first modified version of the liquid ejection head shown in FIG. 1. This modification is different from the liquid ejection head shown in FIG. 1 in that the small hole 7a of the restrictor portion 7 is tapered so that it is greater in diameter on the liquid path side, or the inward side, than on the ejection outlet plane 5q side. Even if the small hole 7a of the restrictor portion 7 is tapered as described above, the effect similar to that of the liquid ejection head shown in FIG. 1 can be obtained, as long as the above described relationships, that is, So$\leq$Sh, c$\leq$e, and/or c$\leq$d, are satisfied. Incidentally, FIG. 3 shows a small hole 7a, the diameter of which gradually reduces from the liquid path 3 side toward the ejection outlet plane 5a. However, the taper of the small hole 7a may be such that the diameter of the small hole 7a gradually reduces from the ejection outlet plane 5a toward the liquid path 3 side, or that the diameter of the small hole 7a gradually reduces from the liquid path 3 side toward a given point between the liquid path 3 and the ejection outlet plane 5a, and then, gradually increases from this point toward the ejection outlet plane 5a. Further, the edges of the small hole 7a of the restrictor portion 7 may be rounded. In other words as long as the small hole 7a or the restrictor portion 7 is tapered so that its diameter gradually reduces or increases toward the liquid path or recess, its configuration is optional.

Figure 4:
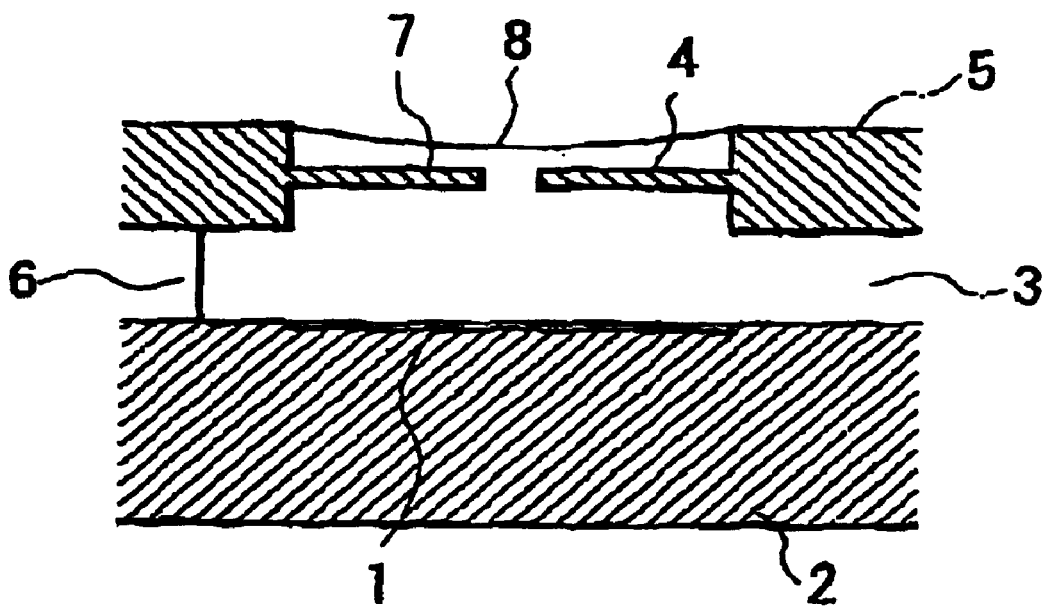
FIG. 4 is a sectional view of the second modified version of the liquid ejection head shown in FIG. 1.

FIG. 4 shows the second modification of the liquid ejection head shown in FIG. 1. The liquid ejection head shown in FIG. 4 is different from the liquid ejection head shown in FIG. 1 in that the restrictor portion 7 is positioned between the outward edge of the ejection outlet 4 of the ejection outlet plate 5 and the top surface of the regulating member 6 for defining the height of the liquid path 3. Even if the position of the restrictor portion 7 in the ejection outlet 4 is changed to a position recessed from the ejection outlet plane 5a, the effect similar to that realized by the liquid ejection outlet shown in FIG. 1 can be realized as long as the above described relationships: So$\leq$Sh, c$\leq$e, and/or c$\leq$d, are satisfied.

FIG. 5 shows the third modification of the liquid ejection head shown in FIG. 1. In the liquid ejection head shown in FIG. 5, the restrictor portion 7 is provided with a plurality of small holes 7a, which oppose a single heater 1. With the provision of this structural arrangement, in which each ejection outlet 4 is provided with the plurality of small holes 7a, not only can the effect similar to that described above be obtained, but also a plurality of liquid droplets can be simultaneously ejected from each ejection outlet 4.

Incidentally, not only can the structural arrangements in the above described first to third modifications be individually employed to a liquid ejection head in accordance with the present invention, but also in optional combination as they fit.

A liquid ejection head in accordance with the present invention ejects (inclusive of atomizing) liquid in the form of an remarkably small droplet, being therefore highly recommendable as the liquid ejection head for such an apparatus as an ink jet recording head in the field of ink jet recording and a liquid medicine inhaler head in the field of medicine.

When a liquid ejection in accordance with the present invention is employed as an ink jet recording head, its ejection outlets are disposed in a single or plurality of straight lines, and as for the liquid to be ejected, recording liquid such as ink, or surface treatment liquid adhered to a recording sheet, prior to ink ejection, to prevent ink from bleeding through the recording sheet, are used. The direction in which ejection outlets are aligned and/or the length of the line in which the ejection outlets are aligned may be varied as necessary to create an ink jet recording head for a serial type ink jet recording apparatus, or an ink jet recording head for a line type ink jet recording apparatus. In particular, when a liquid ejection head in accordance with the present invention is employed as an ink jet recording head for a serial type ink jet recording apparatus, the liquid ejection head, and the container in which the recording liquid to be supplied to the liquid ejection head is held, may be structured in the form of a cartridge so that they can be united or separated.

INDUSTRIAL APPLICABILITY

As described above, a liquid ejection head in accordance with the present invention can be used for ejecting recording ink in the field of ink jet recording.

Further, a liquid ejection head in accordance with the present invention can also be used as a head for a liquid medicine inhaling apparatus. In such a case, the liquid ejection head is structured so that it can be connected to a liquid medicine dispenser. As for the medicine to be ejected, there are: proteinaceous formulations, such as insulin, human growth hormone, and gonadotropic hormone; nicoline; anesthetic; etc.

What is claimed is:
1. A liquid ejection head comprising:
   a liquid flow path;
   an ejection outlet-forming member, which comprises a part of a wall of said liquid flow path and which forms an ejection outlet for ejecting a droplet of liquid, the ejection outlet having a recessed portion recessed from a plane in which the ejection outlet is formed;
   a heat generating element, provided at a position opposed to the ejection outlet, for generating a bubble in the liquid by application of heat to the liquid;
   a restrictor portion provided at the recessed portion of the ejection outlet, wherein the liquid forms a meniscus and is retained in the ejection outlet such that said restrictor portion is within the liquid, wherein said restrictor portion has an opening and defines an entirety of a closed periphery of the opening, and wherein an area So of the opening of said restrictor portion and a surface area Sh of said heat generating element satisfy the following inequality:

So≦Sh.

2. A liquid ejection head comprising:

a liquid flow path;

an ejection outlet-forming member, which comprises a part of a wall of said liquid flow path and which forms an ejection outlet for ejecting a droplet of liquid, the ejection outlet having a recessed portion recessed from a plane in which the ejection outlet is formed;

an energy generating element, provided at a position opposed to the ejection outlet, for generating ejection energy to be applied to the liquid;

a restrictor portion provided at the recessed portion of the ejection outlet, wherein the liquid forms a meniscus and is retained in the ejection outlet such that said restrictor portion is within the liquid, wherein said restrictor portion has an opening and defines an entirety of a closed periphery of the opening, and wherein a thickness c of said restrictor portion and a height e of said liquid flow path measured in a direction in which the ejection outlet and said energy generating element face each other satisfy the following inequality:

c≦e.

3. A liquid ejection head according to claim 2, wherein an area So of the opening of said restrictor portion and a surface area Sh of said energy generating element satisfy the following inequality:

So≦Sh.

4. A liquid ejection head comprising:

a liquid flow path;

an ejection outlet-forming member, which comprises a part of a wall of said liquid flow path and which forms an ejection outlet for ejecting a droplet of liquid, the ejection outlet having a recessed portion recessed from a plane in which the ejection outlet is formed;

an energy generating element, provided at a position opposed to the ejection outlet, for generating ejection energy to be applied to the liquid;

a restrictor portion provided at the recessed portion of the ejection outlet, wherein the liquid forms a meniscus and is retained in the ejection outlet such that said restrictor portion is within the liquid, wherein said restrictor portion has an opening and defines an entirety of a closed periphery of the opening, and wherein a thickness c of said restrictor portion and a thickness d of said ejection outlet-forming member, measured between a plane in which the ejection outlet is formed and a plane of said restrictor portion, satisfy the following inequality:

c≦d.

5. A liquid ejection head according to claim 4, wherein an area So of the opening of said restrictor portion and a surface area Sh of said energy generating element satisfy the following inequality:

So≦Sh.

6. A liquid ejection head according to claim 4 or 5, wherein a height e of said liquid flow path, measured in a direction in which the ejection outlet and said energy generating element face each other, satisfies the following inequality:

c≦e.

7. A liquid ejection head according to claim 6, wherein said energy generating element is a heat generating element.

8. A liquid ejection head according to claim 6, wherein said restrictor portion is disposed in a middle in a direction of a thickness of said ejection outlet-forming member.

9. A liquid ejection head according to claim 6, wherein a diameter of the opening of said restrictor portion changes along a direction of ejection of the liquid through the ejection outlet.

10. A liquid ejection head according to claim 6, wherein the opening of said restrictor portion includes a plurality of fine bores.

11. A liquid ejection head according to claim 6, wherein the liquid is a recording liquid usable for ink jet recording.

12. A liquid ejection head according to claim 6, wherein the liquid is a medicine to be inhaled into a lung.

* * * * *

UNITED STATES PATENT AND TRADEMARK OFFICE
CERTIFICATE OF CORRECTION

PATENT NO. : 6,926,392 B2
DATED : August 17, 2005
INVENTOR(S) : Toshiaki Sasaki et al.

It is certified that error appears in the above-identified patent and that said Letters Patent is hereby corrected as shown below:

Column 1,
Line 3, "bead" should read -- head --.

Column 3,
Line 30, "docs" should read -- does --.
Line 59, "FIG. 1 shows" should read -- FIGS. 1A and 1B show --.
Lines 60 and 62, "FIG. 1(a)" should read -- FIG. 1A --.
Line 61, "FIG. 1(b)" should read -- FIG. 1B --.
Lines 64 and 67, "FIG. 1" should read -- FIGS. 1A and 1B --.

Column 4,
Lines 24 and 56, "FIG. 1" should read -- FIGS. 1A and 1B --.
Lines 40 and 59, "FIG. 1," should read -- FIGS. 1A and 1B, --.
Lines 45 and 52, "FIG. 1," should read -- FIG. 1B, --.
Line 55, "FIG. 2 shows" should read -- FIGS. 2A-2D show --.
Line 63, "FIG. 2(a)," should read -- FIG. 2A, --.

Figure 5A:
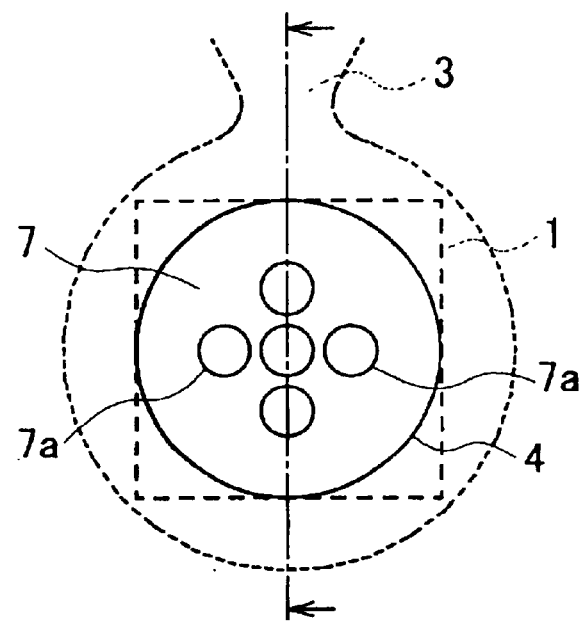
FIG. 5A is a plan view of the third modified version of the liquid ejection head shown in FIGS. 1A and 1B.
Figure 5B:
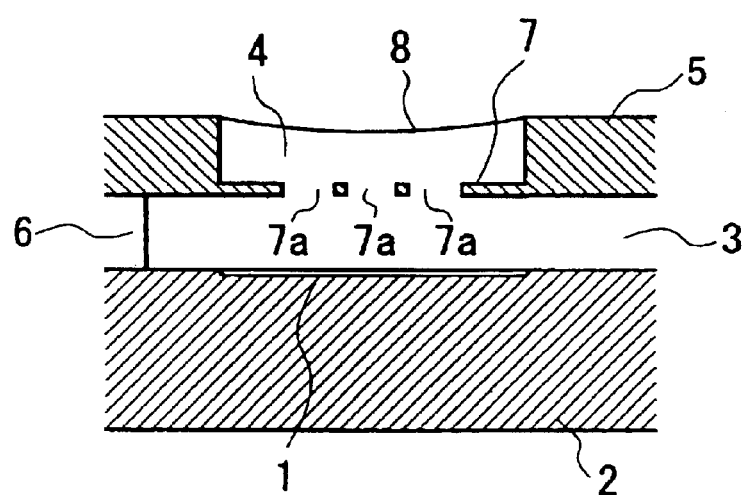
FIG. 5B is a sectional view thereof.

Column 5,
Line 9, "portion" should read -- position --.
Lines 28, 53 and 67, "FIG. 1." should read -- FIGS. 1A and 1B. --.
Line 32, "5q" should read -- 5a --.
Lines 29, 35, 55 and 63, "FIG. 1" should read -- FIGS. 1A and 1B --.
Line 66, "FIG. 5 shows" should read -- FIGS. 5A and 5B show --.

UNITED STATES PATENT AND TRADEMARK OFFICE
CERTIFICATE OF CORRECTION

PATENT NO. : 6,926,392 B2
DATED : August 17, 2005
INVENTOR(S) : Toshiaki Sasaki et al.

It is certified that error appears in the above-identified patent and that said Letters Patent is hereby corrected as shown below:

Column 6,
Line 1, "FIG. 5," should read -- FIGS. 5A and 5B, --.
Line 15, "an" should read -- a --.
Line 20, "in" should read -- head in --.
Line 26, "are" should read -- is --.

Signed and Sealed this

Twenty-first Day of February, 2006

JON W. DUDAS
*Director of the United States Patent and Trademark Office*

UNITED STATES PATENT AND TRADEMARK OFFICE
CERTIFICATE OF CORRECTION

PATENT NO. : 6,926,392 B2
DATED : August 9, 2005
INVENTOR(S) : Toshiaki Sasaki et al.

It is certified that error appears in the above-identified patent and that said Letters Patent is hereby corrected as shown below:

Column 1,
Line 3, "bead" should read -- head --.

Column 3,
Line 30, "docs" should read -- does --.
Line 59, "FIG. 1 shows" should read -- FIGS. 1A and 1B show --.
Lines 60 and 62, "FIG. 1(a)" should read -- FIG. 1A --.
Line 61, "FIG. 1(b)" should read -- FIG. 1B --.
Lines 64 and 67, "FIG. 1" should read -- FIGS. 1A and 1B --.

Column 4,
Lines 24 and 56, "FIG. 1" should read -- FIGS. 1A and 1B --.
Lines 40 and 59, "FIG. 1," should read -- FIGS. 1A and 1B, --.
Lines 45 and 52, "FIG. 1," should read -- FIG. 1B, --.
Line 55, "FIG. 2 shows" should read -- FIGS. 2A-2D show --.
Line 63, "FIG. 2(a)," should read -- FIG. 2A, --.

Column 5,
Line 9, "portion" should read -- position --.
Lines 28, 53 and 67, "FIG. 1." should read -- FIGS. 1A and 1B. --.
Line 32, "5q" should read -- 5a --.
Lines 29, 35, 55 and 63, "FIG. 1" should read -- FIGS. 1A and 1B --.
Line 66, "FIG. 5 shows" should read -- FIGS. 5A and 5B show --.

UNITED STATES PATENT AND TRADEMARK OFFICE
CERTIFICATE OF CORRECTION

PATENT NO. : 6,926,392 B2
DATED : August 9, 2005
INVENTOR(S) : Toshiaki Sasaki et al.

It is certified that error appears in the above-identified patent and that said Letters Patent is hereby corrected as shown below:

<u>Column 6,</u>
Line 1, "FIG. 5," should read -- FIGS. 5A and 5B, --.
Line 15, "an" should read -- a --.
Line 20, "in" should read -- head in --.
Line 26, "are" should read -- is --.

This certificate supersedes Certificate of Correction issued February 21, 2006.

Signed and Sealed this

Fourth Day of April, 2006

JON W. DUDAS
*Director of the United States Patent and Trademark Office*